United States Patent
Hu et al.

(10) Patent No.: US 11,207,440 B2
(45) Date of Patent: Dec. 28, 2021

(54) VOLATILE COMPOSITION DISPENSER WITH INCREASED MEMBRANE EXPOSURE AND VOLATILE COMPOSITION WEIGHT LOSS

(71) Applicant: The Procter & Gamble Company, Cincinnati, OH (US)

(72) Inventors: Hua Hu, Mason, OH (US); Rahul Vyas, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 187 days.

(21) Appl. No.: 16/595,598

(22) Filed: Oct. 8, 2019

(65) Prior Publication Data

US 2020/0038539 A1 Feb. 6, 2020

Related U.S. Application Data

(63) Continuation of application No. 15/582,841, filed on May 1, 2017, now Pat. No. 10,471,168.

(Continued)

(51) Int. Cl.
*A61L 9/00* (2006.01)
*A24F 25/00* (2006.01)
(Continued)

(52) U.S. Cl.
CPC .............. *A61L 9/12* (2013.01); *A01M 1/2044* (2013.01); *A01M 1/2055* (2013.01); *A61L 9/127* (2013.01); *A61L 2209/131* (2013.01)

(58) Field of Classification Search
CPC ....... A61L 9/12; A01M 1/2027; A01M 29/12; A61M 21/02
(Continued)

(56) References Cited

U.S. PATENT DOCUMENTS 4,382,548 A 5/1983 Van
4,526,320 A 7/1985 Von
(Continued)

FOREIGN PATENT DOCUMENTS

CN 200990316 Y 12/2007
EP 1039218 A1 9/2000
(Continued)

OTHER PUBLICATIONS

All Office Actions, U.S. Appl. No. 15/582,841.
(Continued)

*Primary Examiner* — Monzer R Chorbaji
(74) *Attorney, Agent, or Firm* — Abbey A. Lopez

(57) ABSTRACT

A volatile composition dispenser includes a housing having opposing first and second walls that are joined along their peripheries to one another. The first wall has an aperture and the second wall has a plurality of apertures. Within the housing, rests a volatile composition cartridge and a gap, which exists between the cartridge and a bottom surface of the housing, wherein said bottom surface is formed from a joinder of a base portion of one or both of the first and second walls, and wherein, upon activation, the exposure percentage of the dispenser is from about 40% to about 90%; wherein at least about 60% of the total surface area of the plurality of apertures results from individual apertures of said plurality that each have an area of at least 30 mm² and an aspect ratio of at least about 1:2. Dispenser of a similar housing, cartridge, and gap when is activated by a user and thirty days after said activation, exhibits about 70% to 90% weight loss of said volatile composition of a partially exposed membrane of a fully exposed membrane.

18 Claims, 9 Drawing Sheets

Related U.S. Application Data

(60) Provisional application No. 62/330,871, filed on May 3, 2016.

(51) Int. Cl.
 *A61L 9/12* (2006.01)
 *A01M 1/20* (2006.01)

(58) Field of Classification Search
 USPC .............. 422/1, 5, 306; 239/34; 261/DIG. 88
 See application file for complete search history.

(56) References Cited

U.S. PATENT DOCUMENTS

| | | | |
|---|---|---|---|
| 4,572,375 A | 2/1986 | Baer | |
| 5,875,968 A | 3/1999 | Miller | |
| 6,119,958 A | 9/2000 | De | |
| 6,179,139 B1 | 1/2001 | Heilman | |
| 8,622,209 B2 | 1/2014 | Isaac | |
| 8,740,110 B2 * | 6/2014 | Gruenbacher | A61L 9/127 239/34 |
| 8,931,711 B2 | 1/2015 | Gruenbacher et al. | |
| 8,978,999 B2 | 3/2015 | Lesniak | |
| 9,015,989 B1 | 4/2015 | Zeamer | |
| 9,439,993 B2 | 9/2016 | Gruenbacher et al. | |
| 2006/0175425 A1 | 8/2006 | Mcgee | |
| 2006/0191189 A1 | 8/2006 | Mayo | |
| 2009/0302128 A1 | 12/2009 | Zobele | |
| 2010/0310429 A1 | 12/2010 | Kanner | |
| 2010/0314461 A1 | 12/2010 | Gruenbacher et al. | |
| 2011/0180621 A1 | 7/2011 | Gruenbacher et al. | |
| 2012/0267279 A1 | 10/2012 | Lesniak | |
| 2012/0275932 A1 | 11/2012 | Sharma | |
| 2012/0312706 A1 | 12/2012 | Isaac | |
| 2014/0103136 A1 | 4/2014 | Sidawi | |
| 2014/0110495 A1 | 4/2014 | Gundy | |
| 2015/0060565 A1 | 3/2015 | Furner | |
| 2016/0354505 A1 | 12/2016 | Gruenbacher et al. | |
| 2017/0043047 A1 | 2/2017 | Beck et al. | |
| 2017/0319731 A1 | 11/2017 | Hasenoehrl | |
| 2017/0319732 A1 | 11/2017 | Hasenoehrl | |
| 2017/0319733 A1 | 11/2017 | Hu | |
| 2017/0319734 A1 | 11/2017 | Deflorian | |

FOREIGN PATENT DOCUMENTS

| | | |
|---|---|---|
| JP | S52103951 U | 8/1977 |
| JP | S6195080 U | 6/1986 |
| JP | S63184040 U | 11/1988 |
| JP | 2001190206 A | 7/2001 |
| JP | 2002113086 A | 4/2002 |
| JP | 2009032402 A | 2/2009 |
| JP | 2009208777 A | 9/2009 |
| JP | 2013183701 A | 9/2013 |
| WO | WO 98/16262 A1 | 4/1998 |
| WO | 2006061803 A1 | 6/2006 |
| WO | WO 2006/061802 A1 | 6/2006 |
| WO | 2009054597 A1 | 4/2009 |
| WO | 2010120960 A1 | 10/2010 |

OTHER PUBLICATIONS

PCT Search Report PCT/US2017/030713; dated Jul. 26, 2017; 13 Pages.
PCT Search Report PCT/US2017/030715; dated Jul. 26, 2017; 14 Pages.
PCT Search Report PCT/US2017/030716; dated Jul. 20, 2017; 13 Pages.
PCT Search Report PCT/US2017/030717; dated Sep. 11, 2017; 15 Pages.
All Office Actions for U.S. Appl. No. 15/582,828.
All Office Actions for U.S. Appl. No. 15/582,834.
All Office Actions for U.S. Appl. No. 15/582,849.
U.S. Appl. No. 15/582,828, filed May 1, 2017, Hasenoehrl, et al.
U.S. Appl. No. 15/582,841, filed May 1, 2017, Hu, et al.
U.S. Appl. No. 15/582,834, filed May 1, 2017, Hasenoehrl, et al.
U.S. Appl. No. 15/582,849, filed May 1, 2017, Deflorian, et al.
All Office Actions; U.S. Appl. No. 29/707,597.
U.S. Appl. No. 29/707,597, filed Sep. 30, 2019, Richard Lee Lane et al.

* cited by examiner

VOLATILE COMPOSITION DISPENSER WITH INCREASED MEMBRANE EXPOSURE AND VOLATILE COMPOSITION WEIGHT LOSS

FIELD OF THE INVENTION

The invention relates to the field of devices suitable for dispensing volatile compositions like fragrances into the air of a controlled environment, e.g., a room.

BACKGROUND OF THE INVENTION

It is well known that a device may be used to provide a pleasant scent or other emanated material for olfactory sensing within a room of a home, office, or other contained domestic environment. Typically, such devices perpetuate a volatile composition, e.g., fragrance, odor masker, medicine, disinfectant, deodorizer, insect repellant, aromatherapy material, vaporized medication, or other volatile composition by either an energized or non-energized means. In the case of an energized means, the volatile composition's perpetuation within the room is heightened by the use of electricity to power the device and usually the perpetuation is intermittent. For non-energized devices, they are usually activated by some type of user operation. This activation may involve removal or peeling away of an impermeable layer from a container for the volatile composition such that a release of the composition occurs or it may involve mere exposure of the volatile composition by opening up the device to the environment.

U.S. Pat. No. 8,696,982 B2 discloses a method for delivering a volatile material to the atmosphere in a continuous, non-energized manner. This method involves providing a delivery engine comprising a reservoir of volatile material, a microporous membrane enclosing the reservoir, a rupturable substrate enclosing the reservoir, a flow path between the substrate and the membrane, and a rupture element of a particular configuration.

Similarly, U.S. Pat. No. 8,740,110 B2 discloses an apparatus for delivering a volatile material wherein the apparatus comprises a delivery engine that includes a reservoir for the material, a rupturable substrate secured to the reservoir, a rupture element positioned adjacent to the substrate, a membrane of a certain porosity and thickness wherein when the element is actuated causing the breach of the substrate which in turn causes the material to cross to the membrane for diffusion to the atmosphere, and a housing comprising a base, a shell, and a hollowed core, wherein the core comprises a notch for compressing the rupture element upon insertion of the delivery engine in the housing.

Neither the above described method nor the apparatus, however, focuses on providing consumers with a potential benefit that may be derived by increasing the exposure of a membrane wetted with a volatile composition to the environment by means of an improved housing. It is appreciated that there are devices known in the fragrance provision spectrum that include membranes that are fully exposed or nearly fully exposed to their respective environments to be treated. None, however, have been able to provide extended and heightened release of such fragrances while still providing effective containment of the membrane for aesthetic and safety purposes. It should also be noted that neither of the abovementioned references focuses on the potential benefit of increased volatile composition weight loss of cartridges included therein wherein that is subjected to such an increased exposure in a device.

Therefore, there still exists a need for a device or dispenser of volatile compositions that while being non-energized is capable of delivering a continuous but heightened volatile composition delivery to an environment as a result of increased wetted membrane exposure.

SUMMARY OF THE INVENTION

According to an embodiment of the present invention, there is a volatile composition dispenser comprising:
  a) a housing having opposing first and second walls that are joined along their peripheries to one another, wherein said first wall has an aperture and wherein said second wall has a plurality of apertures;
  b) a volatile composition cartridge disposed within the housing between said first and second walls;
  c) a gap, which exists between said cartridge and a bottom surface of the housing, wherein said bottom surface is formed from a joinder of a base portion of one or both of the first and second walls, and
  wherein, upon activation, the exposure percentage is from about 40% to about 90%; wherein at least about 60% of the total surface area of the plurality of apertures results from individual apertures of said plurality that each have an area of at least 30 mm$^2$ and an aspect ratio of at least about 1:2.

According to another embodiment of the present invention, there is a volatile composition dispenser comprising:
  a) a housing having opposing first and second walls that are joined along their peripheries to one another, wherein said first wall has an aperture and wherein said second wall has a plurality of apertures wherein at least about 60% of a total surface area of the plurality of apertures results from individual apertures that have an aspect ratio of greater than 1:2;
  b) a volatile composition cartridge comprising a membrane wherein said cartridge is disposed within the housing between said first and second walls; and
  c) a gap, which exists between said cartridge and a bottom surface of the housing, wherein said bottom surface is formed from a joinder of a base portion of one or both of the first and second walls; and
wherein said dispenser is activated by a user and thirty days after said activation, there is about 70% to 90% weight loss of said volatile composition of a partially exposed membrane of a fully exposed membrane.

DETAILED DESCRIPTION OF THE INVENTION

The present invention relates to a volatile composition dispenser for the delivery of a volatile material to the atmosphere, particularly within an enclosed space. This dispenser is suitable for various uses where volatiles are useful. For instance, such uses, include but are not limited to, air freshening, deodorization, odor elimination, malodor counteraction, pest control, insect control, insect repelling, medicines/medicaments, disinfectants, sanitization, mood enhancement, aromatherapy aid, or any other use which requires a volatile composition that acts to condition, modify, or otherwise change the atmosphere or the environment. For the purposes of illustrating the present invention in detail, but without intending to limit the scope of the invention, the invention will be described as a volatile composition dispenser for delivering a liquid, gel, or even solid particle compositions containing perfume raw materials.

This dispenser is targeted at providing a framework that allows for increased exposure of a membrane that has been wetted with a volatile composition, i.e., a scented material. One of the disadvantages of increased exposure of the membrane is the likelihood of mishandling by a user which might result in user contact with the membrane. Therefore, there is a balance that must be achieved to provide a fairly open housing which promotes an increased exposure to the membrane while also providing an safe, user friendly, and aesthetically pleasing device for provision of the selected scent or material to the environment.

Figure 1:
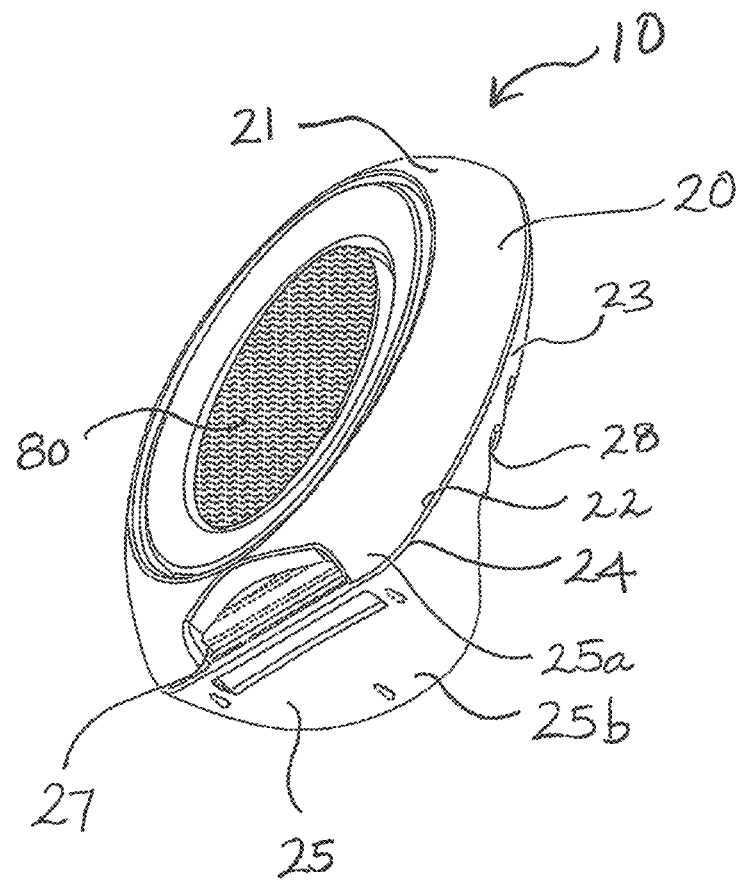
FIG. 1 is a front perspective view of a volatile composition dispenser according to an embodiment.
Figure 2:
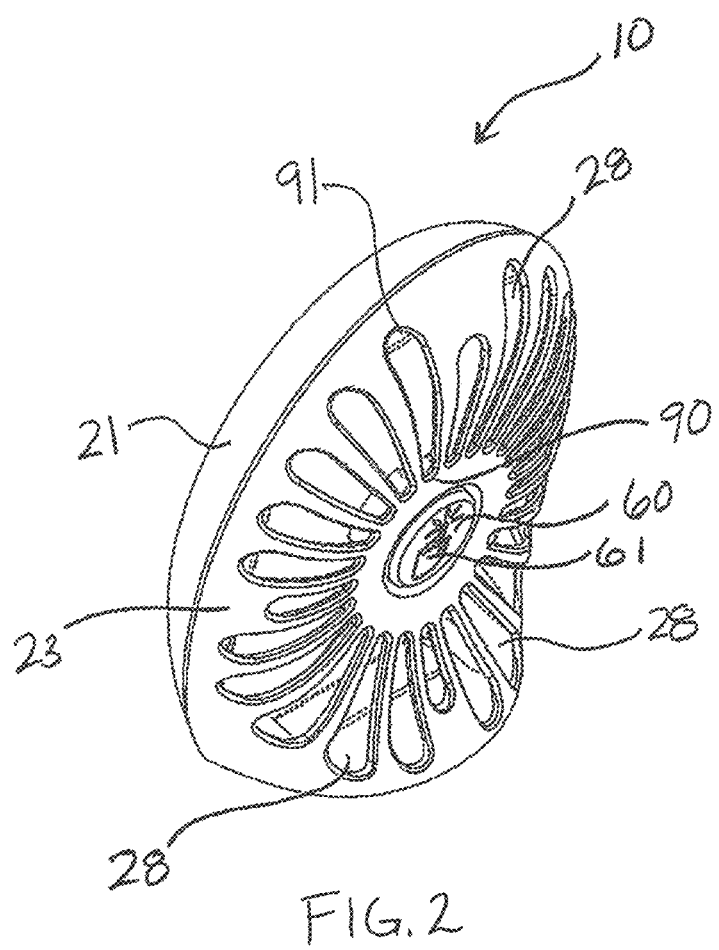
FIG. 2 is a rear perspective view of the volatile composition dispenser shown in FIG. 1.

FIG. 1 shows a front perspective view of an embodiment of a volatile composition dispenser 10 of the present invention while FIG. 2 shows a rear perspective view of this embodiment. The dispenser 10 depicted comprises a housing 20 having a first wall 21 which opposes a second wall 23. The constituents of the housing 20, including the first and second walls may be made from plastic, bamboo, wood, glass, shell, pulp, metals, or metalloids. It is also foreseeable in certain embodiments that the selected material of the walls may be recyclable or even made from recyclable materials. Any of the components of the housing which include the first and second walls as well as the button and button channel (which are discussed later in reference to FIG. 4) may be molded via thermal means, injection, or by blowing. These first and second walls are joined to each other along their respective peripheries 22, 24. These walls may be joined to one another by various mechanisms including snap fit connectors, glue, or one or more latches that mechanically attaches one of the walls to the other. The first wall 21 and second wall 23 may be individually convex and may even be so convex as to form two hemispherical walls separately and a sphere shaped dispenser when joined to one another. In the depicted embodiment, however, the first wall 21 and second wall 23 are each curvedly contoured in an elliptical shell form. Therefore, in this instance, they form an elliptical shaped disc housing and dispenser. One might say that the first and second walls of this embodiment are shell shaped. The first wall 21 includes a window 80 and a primary aperture 27. In this embodiment, the primary aperture 27 is disposed near a base portion 23 of the first wall. The primary aperture may vary in size but may have an area from about 30 mm$^2$, 40 mm$^2$, 50 mm$^2$, 60 mm$^2$, 70 mm$^2$, 80 mm$^2$, 90 mm$^2$ or even 100 mm$^2$ to about 120 mm$^2$, 130 mm$^2$, 140 mm$^2$, 150 mm$^2$, 160 mm$^2$, 170 mm$^2$, or 180 mm$^2$. In this embodiment, the primary aperture 27 is about 110 mm$^2$.

The window 80 is useful for providing a user with the ability to be able to visually gauge the volume of the volatile composition within the receptacle of the cartridge. This window 80 easily accommodates a rear or bottom surface of a cartridge 50 (referred to in FIG. 3) and in most cases it will be transparent or translucent to facilitate in the viewing of the volume. This window 80 may take on various shapes. In this embodiment, it is oval shaped but it may be rectangular, circular, triangular, or other asymmetric shapes that allow a user sufficient sight of the receptacle. The window 80 may also be of variable sizing. In an oval or elliptical configuration of the dispenser, the length may range from about 3 cm, 3.5 cm, 4 cm, 4.5 cm, or 5 cm to about 7 cm, 7.5 cm, 8 cm, 8.5 cm or 9 cm, while the width ranges from about 3 cm, 3.5 cm, or 4 cm to about 5 cm, 5.5 cm, 6 cm, 6.5 cm, 7 cm, 7.5 cm, or 8 cm. In one embodiment, the length of the housing is 6 cm while the width is 4.5 cm. The volatile composition may vary in color from dispenser to dispenser. The color of the composition may be coordinated with the color of the housing or an indicia on the button to promote a fragrance theme. For instance, the composition may be blue while the indicia on the button, e.g., a hand print, may also be blue to indicate an "ocean" or "calming" theme.

Another feature of the present invention is believed to be the operational aspect where the primary aperture 27 cooperates (and possibly to some extent the window 80 also cooperates) with a plurality of apertures 28 that are within the second wall 23 to provide a chimney stack effect which promotes movement of air through the housing even when the dispenser is at rest on a surface within the room which is exposed to the volatile composition once the dispenser is activated.

Although not shown in the figures, the first wall may also comprise a second plurality of apertures around the window. The second plurality of apertures may be of equivalent size to one another and may range in number that is two or greater. It should be noted that these apertures are distinct from the primary aperture as well as the window. Without being limited by theory, the second plurality of apertures likely facilitate in the pass through of air in the dispenser thereby increasing the evaporation of the volatile composition and ultimate provision of the composition into the environment.

Figure 3:
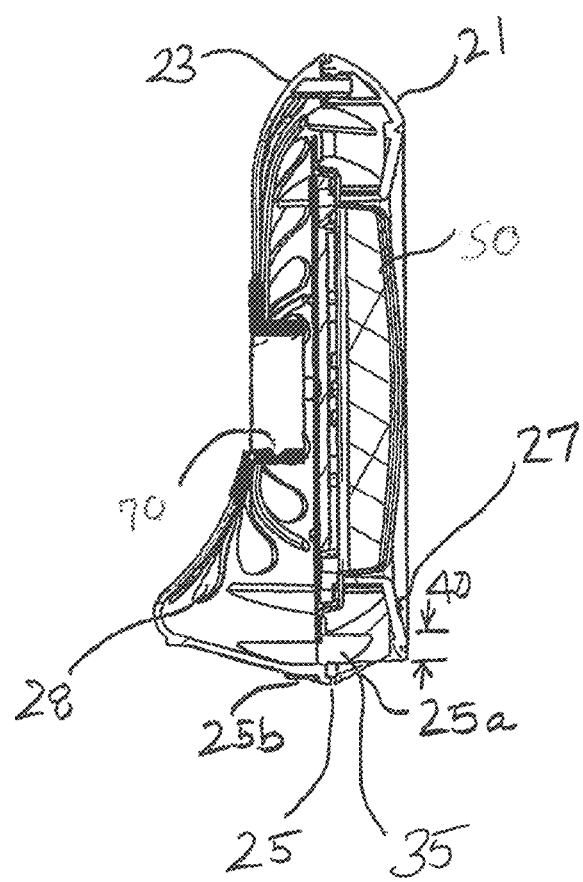
FIG. 3 is a cross section view of a rear frame for a volatile composition dispenser according to the embodiment of FIGS. 1 and 2.
Figure 4:
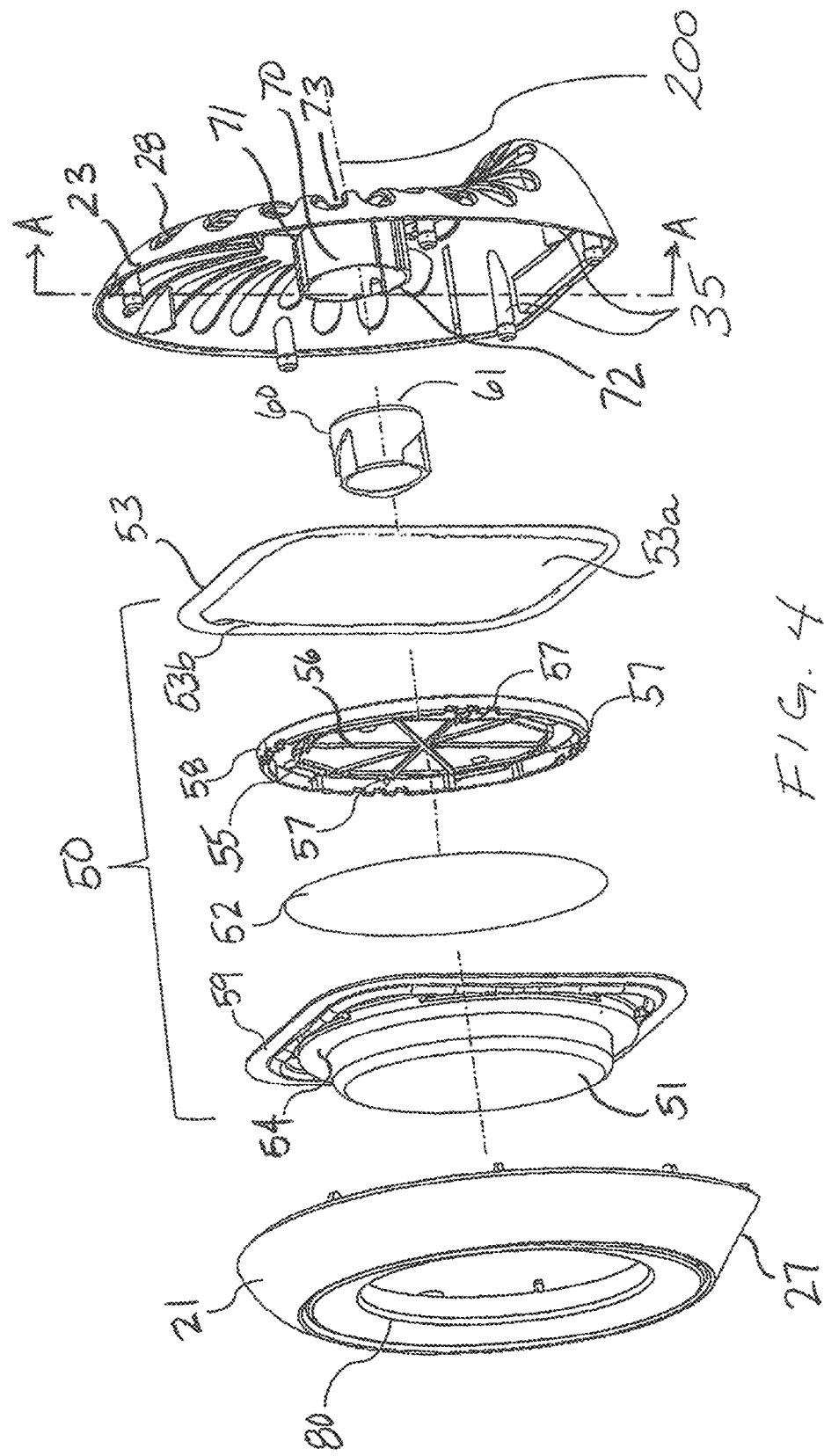
FIG. 4 is a side perspective exploded view of the volatile composition dispenser shown in FIG. 1.

FIG. 3 depicts a cross section view of the dispenser of FIGS. 1 and 2 along A-A (shown in FIG. 4). This allows for appreciation of the volatile composition cartridge 50 and its placement within the housing 20 which results in the formation of the gap 40. This gap 40 is formed from the space that exists and extends between a bottom of the cartridge and a base portion 25 made up one or both of the first wall 22 (25a) and the second wall 24 (25b). The gap is facilitated by supports 35 which are attached to the first and second walls and in effect prop up the cartridge 50 within the housing 20.

The gap 40 may range in height from 0.5 mm, 0.6 mm, 0.7 mm, 0.8 mm, or 0.9 mm to 1.1 mm, 1.2 mm, 1.3 mm, 1.4 mm, 1.5 mm, 1.6 mm, 1.8 mm, or 2 mm. In one embodiment, the gap is about 1 mm high. Without being limited by theory, it is believed that this gap 40 facilitates air flow through the dispenser 10. In particular, air may enter the dispenser in any one of the openings in the first or second wall. For instance, air may flow into the first wall 21 through the aperture 27, through the gap 40, and then over a surface of the cartridge and out through the plurality of apertures 28 of the second wall 23 into the atmosphere. In another instance, air may enter the dispenser in the plurality of apertures and flow across a width or length of the dispenser such that the air flows out of an opposite side of the same second wall 23. In either of these instances, it is envisioned that the primary driver of perpetuation of a volatile composition from the cartridge to the environment is air flow, either diffusive or convective, across a membrane of the cartridge. In preferred embodiments, the primary mechanism of perpetuation of the volatile composition is convective air flow.

FIG. 4 shows an exploded view of the volatile composition cartridge 50. The cartridge 50 comprises a receptacle 51 containing a volatile composition and this composition is sealed within the receptacle 51 by a rupturable substrate 52. The substrate 52 may be any material that is susceptible to rupturing as required by the present invention. Because the rupturable substrate 52 is intended to contain a volatile composition while in storage, it may be made from any barrier material that prevents evaporation of the volatile composition prior to its intended use. Such materials may be impermeable to vapors and liquids. Suitable barrier materials for the rupturable substrate 52 include a flexible film, such as a polymeric film, a flexible foil, or a composite material such as foil/polymeric film laminate. Suitable flexible foils include a metal foil such as a foil comprised of a nitrocellulose protective lacquer, a 20 micron aluminum foil, a polyurethane primer, and 15 g/m2 polyethylene coating (Lidfoil 118-0092), available from Alcan Packaging. Suitable polymeric films include polyethylene terephtalate (PET) films, acrylonitrile copolymer barrier films such as those sold under the tradename Barex® by INOES, ethylene vinyl alcohol, and combinations thereof. It is also contemplated that coated barrier films may be utilized as a rupturable substrate 52. Such coated barrier films include metalized PET, metalized polypropylene, silica or alumina coated film may be used. Any barrier material, whether coated or uncoated, may be used alone and or in combination with other barrier materials.

The receptacle 51 of the cartridge 50 may be configured dimensionally to hold from about 1 ml, 2 ml, 3 ml, or 4 ml to about 6 ml, 10 ml, 20 ml, 30 ml, 40 ml or even 50 ml of a volatile composition. In certain embodiments, the receptacle may contain about 2 ml of a volatile composition. In another embodiment, the receptacle may contain about 6 ml of a volatile composition. In these cases, the composition is likely in liquid form. Further, a shape of the receptacle 51 may be configured to correspond to a shape of the window 80 of the first wall. For example, the receptacle 51 may define a substantially elliptical or oval shape and its width to length ratio may be about 1:2 to 1:2.5.

The volatile composition may be suitable for a variety of uses and may be presented in various forms of a liquid, gel, or solid. Ideally, the volatile composition will be a material that is readily absorbable into a membrane as discussed herein and is easily vaporizable therefrom when into the atmosphere over an extended and continuous period of time. Suitable volatile compositions perfume oils, perfume raw materials, crystalline solids, and combinations thereof.

The volatile composition may be formulated to comprise about 10% to about 100%, by total weight, of volatile materials that each having a VP at 25° C. of less than about 0.01 torr; alternatively about 40% to about 100%, by total weight, of volatile materials each having a VP at 25° C. of less than about 0.1 torr; alternatively about 50% to about 100%, by total weight, of volatile materials each having a VP at 25° C. of less than about 0.1 torr; alternatively about 90% to about 100%, by total weight, of volatile materials each having a VP at 25° C. of less than about 0.3 torr. In one embodiment, the volatile material mixture may include 0% to about 15%, by total weight, of volatile materials each having a VP at 25° C. of about 0.004 torr to about 0.035 torr; and 0% to about 25%, by total weight, of volatile materials each having a VP at 25° C. of about 0.1 torr to about 0.325 torr; and about 65% to about 100%, by total weight, of volatile materials each having a VP at 25° C. of about 0.035 torr to about 0.1 torr. One source for obtaining the saturation vapor pressure of a volatile material is EPI Suite™, version 4.0, available from U.S. Environmental Protection Agency.

The sealing of the substrate 52 occurs along an inner lip 54 of the receptacle 51. The sealing may amount to a mere securing of the substrate to the cartridge. This sealing may result from the use of a means selected from heat, adhesive, mechanical attachment (assuming such is leakproof) like crimping, ultrasonic bonding, or any combination thereof.

A rupturing element 55 is placed next to the rupturable substrate 52 and is biasingly movable to contact the substrate 52 to cause rupturing or puncturing of the substrate 52 when activation occurs. The rupturing element 55 comprises rupturing pins 57 on one or more spring based flexing arms 56 or on a flexing support ring 58 for the arms 56. Each of the rupturing element, arms, pins, and support ring may be formed from molded plastic via injection, pressure, or compression. In certain embodiments, a user may press the button along its longitudinal axis 200 (shown in FIG. 4) to activate the dispenser.

A membrane 53 is placed in a sealing manner over an outer lip 59 of the receptacle 51. The membrane may be a breathable and/or microporous. The membrane may have an average pore size of from 0.01 microns or 0.02 microns to about 0.03, 0.04, 0.05, or 0.06 microns. In a certain embodiment, the average pore size is about 0.02 microns. The membrane has a thickness of about 0.1 mm, 0.15 mm, 0.2 mm, to about 0.3 mm, 0.4 mm, 0.5 mm, 0.6 mm, 0.8 mm, or 1 mm. In a certain embodiment, the thickness may be 0.25 mm. Further, the membrane 53 may be filled with any suitable filler and plasticizer known in the art. Fillers may include finely divided silica, clays, zeolites, carbonates, charcoals, and mixtures thereof. The microporous membrane 53 may be filled with about 50% to about 80%, by total weight, of silica, alternatively about 60% to about 80%, alternatively about 70% to about 80%, alternatively about 70% to about 75%. A thickness of the membrane 53 may be about 0.01 mm to about 1 mm, alternatively between about 0.1 mm to 0.4 mm, alternatively about 0.15 mm to about 0.35 mm, alternatively about 0.25 mm. This membrane 53 is next to the rupturing element 55, effectively providing a covering for the rupturing element 55 within the receptacle 51. Suitable membranes include those which are also ultrahigh molecular weight polyethylene and such materials are commercially available as Daramic™ V5 from Daramic, Soluport® from DSM of the Netherlands, and Teslin™ from PPG Industries. Once the dispenser is activated, the volatile composition spreads out of the receptacle and wets the membrane and is then delivered to the environment. It is intended that the volatile composition be virtually undetectable by a user until such time as activation occurs. Then, once activated, the scent of the volatile composition is quite noticeable and should remain so throughout the life of the dispenser until the volatile composition level is indicated as being fairly low or non-existent within the window 80.

Figure 5:
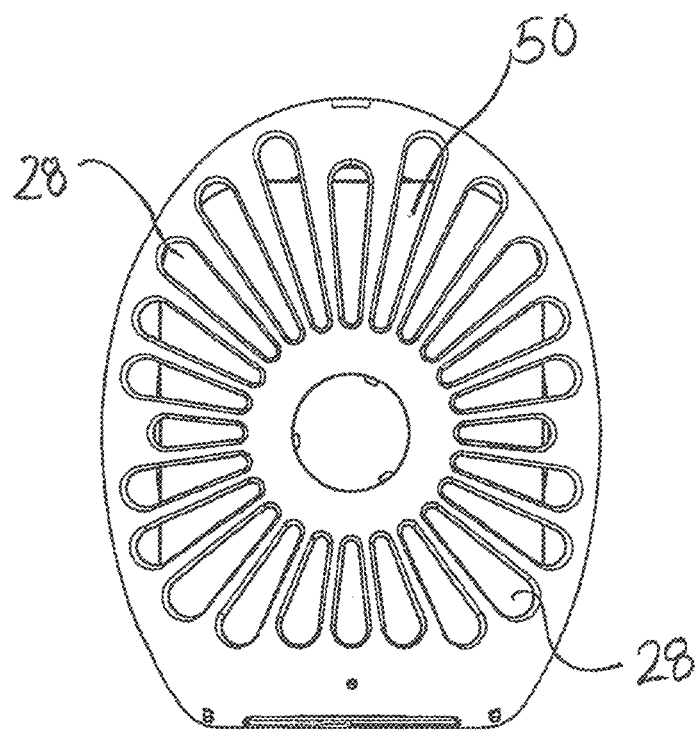
FIG. 5 is a rear view the volatile composition dispenser according to an the embodiment of FIG. 1.

FIG. 5 shows a rear view of the dispenser. From this view, the total surface area of the plurality of apertures 28 can be appreciated. The total surface area of these apertures is determined by adding the surface area of each of the openings on the second wall (excluding the entrance of a button channel where the button is placed). The total surface area of the membrane 51 is measured based on a portion of the membrane's exterior surface which is wettable. In the embodiment of FIGS. 1-5, the total surface area of the plurality of apertures 28 of which there are twenty-four is 2396 $mm^2$ or about 2400 $mm^2$. In FIG. 4, the wettable surface area 53a of the membrane is shown and can be measured as the total exterior surface area of membrane minus an area of the sealed membrane 53b area joined to the outer lip 59 of the receptacle 51. In this embodiment, the sealed membrane area 53b is about 8 $cm^2$ while the total surface area of the membrane is 35 $cm^2$. Therefore, the wettable surface area of the membrane 52a is about 2700 $mm^2$. In practice the total surface area of the membrane 53 may be from about 200 $mm^2$, 1000 $mm^2$, 1500 $mm^2$, 2000 $mm^2$, 2500-$mm^2$, or 3000 $mm^2$ to about 4000 $mm^2$, 5000 $mm^2$, 6000 $mm^2$, or even 10,000 $mm^2$. Suitable membranes include a microporous, ultra-high molecular weight polyethylene (optionally filled with silica), permeable polymeric, thermoplastic, or thermoset materials.

The plurality of apertures 28 has a total surface area that is 90% (i.e., (2396 $mm^2$/2700 $mm^2$)×100%) of the wettable surface area of the membrane. In other embodiments, the ratio or percentage of interest to the present invention is herein referred to as exposure percentage and is derived by taking the total surface area of the plurality of apertures area divided by the wettable surface area. The exposure percentage may range from about 40%, 45%, 50%, 55%, 60%, or even 65% to about 70%, 75%, 80%, or 85%. It should also be noted that it is envisioned that the plurality of apertures 28 of the second wall may actually have a total surface area of that is greater than the total wettable surface of the membrane. That is, the total surface area of the plurality of apertures may be greater than 100%. This may result when the second wall is particularly convex and the surface area of the second wall is severely greater than the surface area of the wettable membrane. In the case where the plurality of apertures 28 includes individual apertures that are large in size and the second wall is convexedly extended, this dynamic may occur.

The plurality of apertures 28 may be of different shapes. A preferred shape, however, is an elongated shape which is shown in this embodiment. These elongated shapes may be selected from the group consisting of resembling flower petals, test tubes, rectangles, triangles, particularly, isosceles triangles, crescent moons, and combinations thereof. In any instance, the elongated nature of the plurality of apertures is important. More specifically, the apertures should have an aspect ratio of at least about 1:2. In other embodiments, this aspect ratio may be at least about 1:3, 1:4, 1:5, or even 1:6. It should be noted that at least about 60% of a total surface area of the plurality of apertures comprise individual apertures that each have an area of at least about 30 $mm^2$ and aspect ratio is at least about 1:2. In other embodiments, it may be at least about 70%, 80%, or 90% or 100% total surface area of the plurality of apertures comprising individual apertures that each has an area of at least about 30 $mm^2$, 35 $mm^2$, 40 $mm^2$, or 42 $mm^2$ to 50 $mm^2$, 60 $mm^2$, 70 $mm^2$, 80 $mm^2$, 90 $mm^2$, 100 $mm^2$, 110 $mm^2$, 120 $mm^2$, 130 $mm^2$, 140 $mm^2$, 150 $mm^2$, or 160 $mm^2$ and an aspect ratio of at least about 1:2, 1:3, 1:4, 1:5, 1:6, 1:7, and up to 1:8. In an embodiment, each of these individual apertures has an area of at least about 42 $mm^2$. The present invention is intended to envision the various combinations of parameters disclosed herein.

It is believed that the configuration of this dispenser allows for an effective and improved convective movement of air flow through the dispenser given the presence of the primary aperture on the first wall, the plurality of apertures on the second wall, and the gap at the base of both. This unique combination of design aspects allow for air to be more readily carried into the dispenser through at least the first wall, through the gap, and up and out of the second wall through the plurality of apertures which provide an increased exposure percentage over devices which are known. Again, the elongated plurality of apertures is critical to this benefit.

Figure 6:
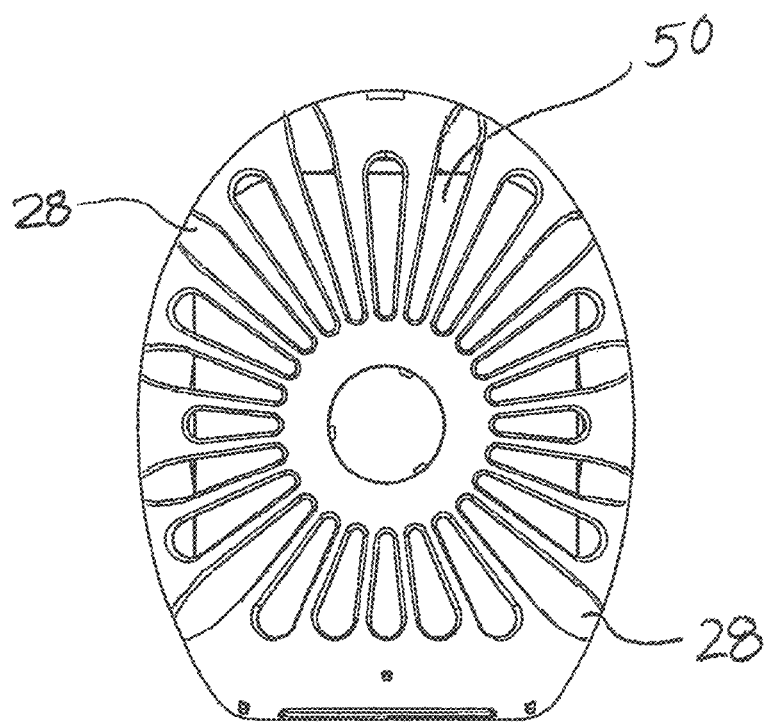
FIG. 6 is a rear view of a volatile composition dispenser of the present invention with an alternate configuration on the second wall.

FIG. 6 shows an alternate configuration of the plurality of apertures 28. In the embodiment of FIG. 1-5, it should be noted that the plurality of apertures 28 shown each have a proximate end 90 that is placed near an opening of a button channel 70 and a distal end 72 that is placed proximate to the periphery 24 of the second wall 23. In the embodiment of FIG. 6, the distal end 91 of one or more of the plurality of apertures 28 may extend to the periphery of the second wall thereby increasing the overall surface area of this group of apertures. This increased area would translate to an increase in the percentage of the total area of the plurality of the apertures versus the wettable surface area of the membrane. This would undoubtedly allow for increased evaporation of the volatile composition into the environment.

It should be noted, however, that FIG. 4 also depicts a button 60 which is slidably disposed within a button channel 70 that extends from an exterior surface 26 of the second wall 23 to an interior of the housing. The button channel 70, which may be tubular, has a proximate end 71 that is flush with the exterior surface 26 of the second wall 23 and a distal end 72 that is a relatively short distance from an outward facing surface of the membrane 53. The button 60 is activated when a user pushes a push surface 61 of the button. This pushing causes the button to slide toward the interior of the dispenser. This pushing on the button amounts to activation of the dispenser. This pushing of the button also causes the button to apply pressure to the membrane 53 which in turn exerts pressure on the rupture element 54. This exerted pressure on the rupture element 55 causes the rupture pins 57 to contact the rupturable substrate 52 and create holes in the substrate through which the volatile composition may now be released for liquid absorption into the membrane for eventual release to the environment by evaporation over an extended period of time. Once this pressure on the rupturable substrate 52 results in the creation of holes in the substrate 52, the user's release of the button allows for the biased rupture element to retract from the substrate returning to the element to an either a post-activation position along the length of the channel or an initial position that is flush with the exterior surface of the second wall or substantially flush with it. This retraction movement of the rupture element allows the holes to be unobstructed and allows for an easier flow of the volatile composition out of the receptacle and to the membrane.

The dispensers of the present invention are characterized by the loss of volatile composition from the cartridge once activated and for a prolonged period of time thereafter. The benefit of this prolonged release is consistent exposure to the volatile composition by those that are in the environment in which the dispenser is placed. In order to determine the efficacy of the dispenser, one might look at the ability of the dispensing device to release the volatile composition. Thus, it is important that this value is measured. For any volatile composition that wets a membrane, an ideal amount of evaporation of that composition occurs in a fully exposed membrane. One objective of the presently claimed dispensers is to come as close to this optimal evaporation as possible as a result of a increased membrane exposure while the dispenser remains aesthetically pleasing for users and safe for those same users and children that might be handling the dispensers. In order to determine the efficacy of the dispenser, one would look at the percentage weight loss of a partially exposed membrane of a fully exposed membrane. First, the cumulative weight loss at a time after activation is calculated.

$$\text{Cumulative Weight Loss at } T_x = W\text{cum}_{Tx} = W_{Ti} - W_{Tx}$$

wherein
$W_{Ti}$=initial weight of volatile composition (mg) prior to activation
$W_{Tx}$=weight of volatile composition (mg) at a designated time (days) after activation This quantity is then used to determine the percentage of cumulative weight loss of the volatile composition as follows.

$$\% \text{ of Cumulative Weight Loss} = \% W\text{cum} = W\text{cum}_{Tx} \div W_{Ti} \times 100\%$$

In order to then determine how the weight loss of the partially exposed membrane of the dispenser compares to a fully exposed membrane, the following calculation is made.

$$\text{Percentage weight loss of partially exposed membrane of fully exposed membrane} = \frac{W\,cum_{Tx} \text{ of partially exposed membrane}}{W\,cum_{Tx} \text{ of } 100\% \text{ exposed membrane}} \times 100\%$$

For these calculations, any volatile composition may be employed. For illustrative purposes as well as for the subsequent examples, a standard perfume composition is disclosed which exhibits the formulation of Table 1.

TABLE 1

| Vapor Pressure 25° C. Low | Vapor Pressure 25° C. High | Perfume Composition Wt Percentage |
| --- | --- | --- |
| 0.001 | 0.01 | 6.45 |
| 0.01 | 0.1 | 19.57 |
| 0.1 | 0.3 | 54.24 |
| 0.3 | 10 | 19.74 |
| | Total | 100 |

The volatile composition, however, may constitute any number of materials.
For calculation of the values detailed herein, one requires the following items:

1. Balance (Scale: Ohaus AA210 S/N 11131122540) or equivalent.
2. Housing of the present invention including a first and second wall
3. Volatile composition cartridges containing 5.5 ml of perfume composition. (If adding a perfume composition by weight, multiply measured density by 5.5 ml to obtain the accurate fill weight.)
4. 3M Scotch Weld Applicator TC and glue, #3797-TC or equivalent.
5. Evaporation rack or equivalent open tray (baker's) rack, covered at the top and shelves spaced at 15 cm or more.
6. Room to accommodate evaporating rack with the following measurements, air flow, temperature/relative humidity or equivalent:
    a) Laboratory Dimensions: 32 feet 4 inches long×72 inches wide×108 inches high or 1,730 ft³
    b) Air Flow (Intake and Exhaust)
       Normal Mode: Average Intake Supply: 103.75 ft³/min±6%
       Average Exhaust: 149.25 ft³/min±6%
       Difference results in negative air pressure: −45.5
       Negative pressure indicates that air supply to laboratory and from an adjacent hallway or room is exhausted through the ventilation system.
    c) Temperature and % Relative Humidity
       Average Temperature: 23°±0.1° C.
       Average % Relative Humidity: 45%±0.5%

Determination of Percentage of Cumulative Weight Loss of Volatile Composition

1. Load the cartridge with the volatile composition in such a way as to provide a sealed cartridge that is not yet wetted. For instance, one may pierce a volatile composition cartridge by cutting in it a hole that allows for insertion of an 18 gauge needle.
2. Fill the cartridge with 5.5 ml of perfume composition. This is equivalent to 5024 mg of the standard perfume composition. The volume may need to be adjusted based on the density of the composition of interest.
3. Seal the insertion hole with hot melt adhesive.
4. Measure and record the weight of the cartridge to three significant figures.
5. Insert the cartridge into the housing and ensure that the cartridge is set correctly within the housing to ensure proper air flow therethrough.
6. Activate the cartridge to wet its membrane. Herein, such activation is achieved by pushing the activation button. There may, however, be equivalent means of activation and wetting the membrane.
7. Pick a time and measure (in mg) and record the cartridge weight daily at the same time for at least thirty days.
8. Determine the percentage of cumulative weight loss of the volatile composition as detailed earlier using the recorded times with their corresponding weights.

The present invention additionally relates to methods of delivering a volatile composition. The method comprises the steps of providing a dispenser as detailed herein in its various characterizations.

EXAMPLES

The following examples and comparative example are not intended to be construed as limiting the present invention since there are many variations which are possible without departing from the spirit and scope.

Example 1

Figure 7A:
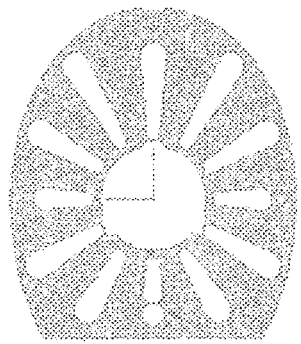
FIG. 7A is a rear view of another embodiment of the dispenser of the present invention.
Figure 7B:
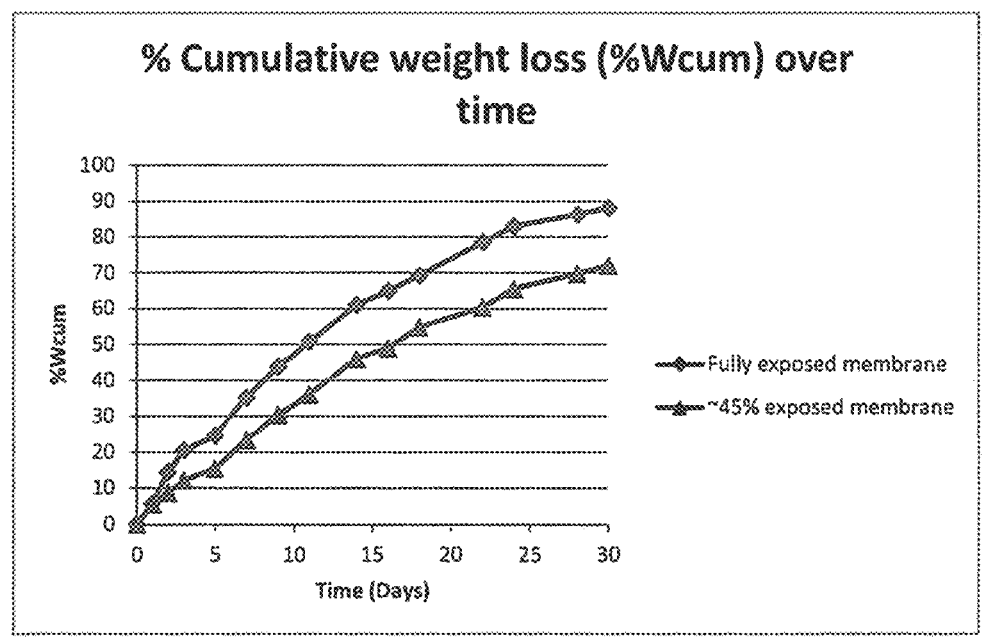
FIG. 7B is a graphical depiction of the volatile composition percentage weight loss of the embodiment of FIG. 7A versus an unhoused cartridge of the present invention.

In this example, the standard perfume formulation is used as the volatile composition. The volatile composition cartridge is configured within a housing having a second wall as shown in FIG. 7A which reflects an approximate exposure percentage of 45% based on the configuration of the plurality of apertures in the second wall. The exposure percentage is calculated as the total area of the plurality of apertures of this second wall of 1188 mm² divided by the entire wettable area of 2700 mm² and multiplied by 100%. The volatile composition is included into the receptacle of the cartridge at an amount of 5.5 ml and this cartridge is inserted between first and second walls. The aspect ratio of the majority of the individual apertures of the plurality of apertures is greater than or equal to 1:2. Per the percentage of cumulative weight loss described herein, % Wcum is measured over a period of 30 days (but includes days 31 and 35) and the volatile composition (perfume) weight loss percentage is shown in FIG. 7B is calculated to be 72% as reported in Table 2 versus the % Wcum of 88% for the fully exposed membrane as shown in Table 3. The percentage weight loss of partially exposed membrane of fully exposed membrane is calculated where $Wcum_{Tx}$ of partially exposed membrane=3620 mg
$Wcum_{Tx}$ of 100% exposed membrane=4430 mg
and is $$\frac{3620 \text{ mg}}{4430 \text{ mg}} \times 100\% = 82\%$$

TABLE 2

~45% Membrane Exposure

| Days | Cumulative Weight Loss (mg) | % Cumulative Weight Loss | Percentage of Wt. Loss of '45% exposed' membrane of fully exposed membrane |
|---|---|---|---|
| 0 | 0 | 0 | — |
| 1 | 280 | 6 | 99 |
| 2 | 440 | 9 | 61 |
| 3 | 613 | 12 | 59 |
| 5 | 777 | 15 | 63 |
| 7 | 1177 | 23 | 66 |
| 9 | 1525 | 30 | 69 |
| 11 | 1816 | 36 | 71 |
| 14 | 2314 | 46 | 75 |
| 16 | 2462 | 49 | 75 |
| 18 | 2754 | 55 | 79 |
| 22 | 3036 | 60 | 77 |
| 24 | 3295 | 66 | 79 |
| 28 | 3504 | 70 | 81 |
| 30 | 3620 | 72 | 82 |
| 31 | 3728 | 74 | 83 |
| 35 | 3964 | 79 | 86 |

TABLE 3

Fully Exposed Membrane (For All Examples Herein)

| Days | Cumulative Weight Loss (mg) | % Cumulative Weight Loss |
|---|---|---|
| 0 | 0 | 0 |
| 1 | 283 | 6 |
| 2 | 725 | 14 |
| 3 | 1032 | 21 |
| 5 | 1234 | 25 |
| 7 | 1775 | 35 |
| 9 | 2203 | 44 |
| 11 | 2555 | 51 |
| 14 | 3067 | 61 |
| 16 | 3264 | 65 |
| 18 | 3482 | 69 |
| 22 | 3947 | 79 |
| 24 | 4173 | 83 |
| 28 | 4336 | 86 |
| 30 | 4430 | 88 |
| 31 | 4476 | 89 |
| 35 | 4627 | 92 |

Example 2

Figure 8A:
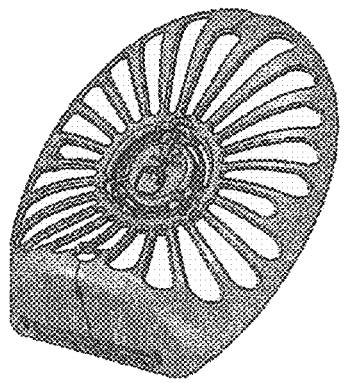
FIG. 8A is a rear view of the embodiment of the dispenser shown in FIG. 1.
Figure 8B:
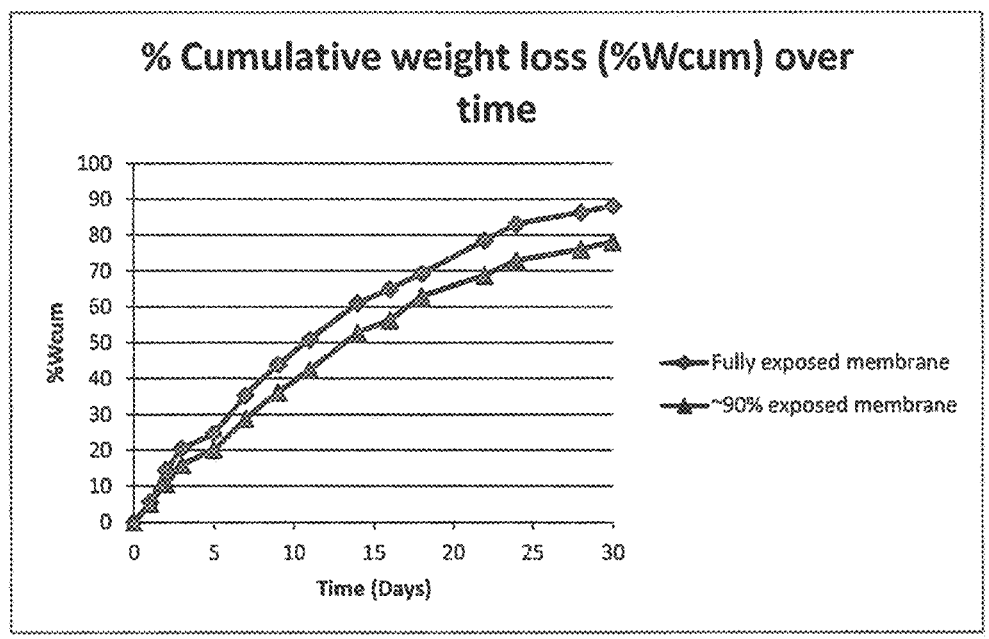
FIG. 8B is a graphical depiction of the volatile composition percentage weight loss of the embodiment of FIG. 8A versus an unhoused cartridge of the present invention.

In this example, the standard perfume formulation is also used as the volatile composition. The volatile composition cartridge is configured within a housing having a second wall as shown in FIG. 8A and as a result the dispenser herein exhibits an exposure percentage of approximately 90% (i.e., (2396 mm²/2700 mm²)×100%) based on the configuration of the plurality of apertures in the second wall. The same amount of the volatile composition is included in this dispenser as is utilized for Example 1. The aspect ratio of the majority of the individual apertures of the plurality of apertures is greater than or equal to 1:2. Per the percentage of cumulative weight loss described herein, % Wcum is measured over a period of 30 days (but includes days 31 and 35) and the volatile composition (perfume) weight loss percentage is shown in FIG. 8B is calculated to be 78% as reported in Table 4 versus the % Wcum of 88% for the fully exposed membrane as shown in Table 3 (in Example 1). The percentage weight loss of partially exposed membrane of fully exposed membrane is calculated where $Wcum_{Tx}$ of partially exposed membrane=3920 mg
$Wcum_{Tx}$ of 100% exposed membrane=4430 mg
and is $$\frac{3920 \text{ mg}}{4430 \text{ mg}} \times 100\% = 88\%$$

TABLE 4

~90% Membrane Exposure

| Days | Cumulative Weight Loss (mg) | % Cumulative Weight Loss | Percentage of Wt. Loss of '90% exposed' membrane of fully exposed membrane |
|---|---|---|---|
| 0 | 0 | 0 | — |
| 1 | 263 | 5 | 93 |
| 2 | 536 | 11 | 74 |
| 3 | 804 | 16 | 78 |
| 5 | 1014 | 20 | 82 |
| 7 | 1449 | 29 | 82 |
| 9 | 1812 | 36 | 82 |
| 11 | 2129 | 42 | 83 |
| 14 | 2651 | 53 | 86 |

TABLE 4-continued

~90% Membrane Exposure

| Days | Cumulative Weight Loss (mg) | % Cumulative Weight Loss | Percentage of Wt. Loss of '90% exposed' membrane of fully exposed membrane |
|---|---|---|---|
| 16 | 2826 | 56 | 87 |
| 18 | 3162 | 63 | 91 |
| 22 | 3452 | 69 | 87 |
| 24 | 3667 | 73 | 88 |
| 28 | 3821 | 76 | 88 |
| 30 | 3920 | 78 | 88 |
| 31 | 4011 | 80 | 90 |
| 35 | 4214 | 84 | 91 |

Comparative Example

Figure 9A:
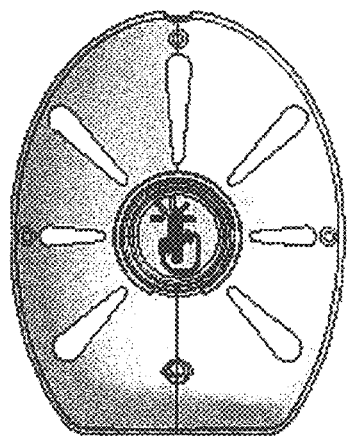
FIG. 9A is a rear view of an embodiment of a dispenser that falls outside of the present invention.
Figure 9B:
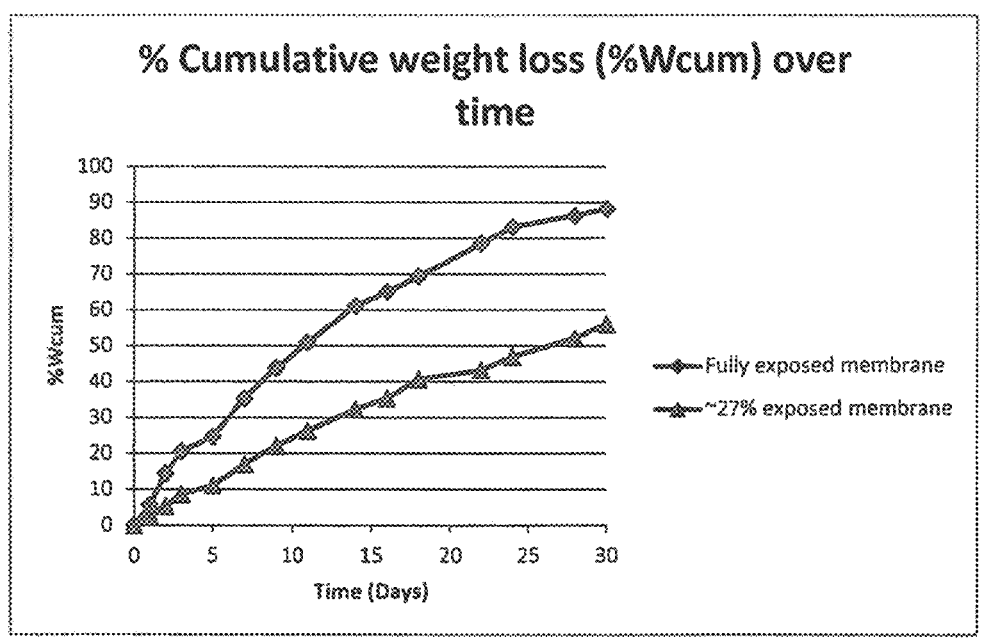
FIG. 9B is a graphical depiction of the volatile composition percentage weight loss of the embodiment of FIG. 9A versus an unhoused cartridge of the present invention.

For comparative purposes, the standard perfume formulation is used in the same amount as in Examples 1 and 2 as the volatile composition but the second wall of the housing of this dispenser is configured as shown in FIG. 9A and exhibits an exposure percentage of 27%, which is calculated as 725 mm²/2700 mm²×100%. The aspect ratio of the majority of the individual apertures of the plurality of apertures is greater than or equal to 1:2 but there are significantly fewer apertures in the second wall. The volatile composition weight loss percentage is measured over a period of 30 days and is shown in FIG. 9B over that time frame. Ultimately, at thirty days (although measured at days 31 and 35) % Wcum is measured and is shown in FIG. 7B is calculated to be 56% as shown in Table 5 below as compared to the % Wcum of 88% for the fully exposed membrane of Table 3 (in Example 1). The percentage weight loss of partially exposed membrane of fully exposed membrane is calculated where
$Wcum_{Tx}$ of partially exposed membrane=2813 mg
$Wcum_{Tx}$ of 100% exposed membrane=4430 mg
and is $$\frac{2813 \text{ mg}}{4430 \text{ mg}} \times 100\% = 63\%$$

TABLE 5

~27% Membrane Exposure

| Days | Cumulative Weight Loss (mg) | % Cumulative Perfume Weight Loss | Percentage of Wt. Loss of '27% exposed' membrane of fully exposed membrane |
|---|---|---|---|
| 0 | 0 | 0 | — |
| 1 | 138 | 3 | 49 |
| 2 | 266 | 5 | 37 |
| 3 | 431 | 9 | 42 |
| 5 | 556 | 11 | 45 |
| 7 | 853 | 17 | 48 |
| 9 | 1108 | 22 | 50 |
| 11 | 1319 | 26 | 52 |
| 14 | 1623 | 32 | 53 |
| 16 | 1774 | 35 | 54 |
| 18 | 2044 | 41 | 59 |
| 22 | 2173 | 43 | 55 |
| 24 | 2360 | 47 | 57 |
| 28 | 2619 | 52 | 60 |
| 30 | 2813 | 56 | 63 |
| 31 | 2876 | 57 | 64 |
| 35 | 3195 | 64 | 69 |

An example is set out below:

A. A volatile composition dispenser comprising:
a) a housing having opposing first and second walls that are joined along their peripheries to one another, wherein said first wall has an aperture and wherein said second wall has a plurality of apertures;
b) a volatile composition cartridge disposed within the housing between said first and second walls;
c) a gap, which exists between said cartridge and a bottom surface of the housing, wherein said bottom surface is formed from a joinder of a base portion of one or both of the first and second walls, and
wherein, upon activation, the exposure percentage is from about 40% to about 90%; wherein at least about 60% of the total surface area of the plurality of apertures results from individual apertures of said plurality that each have an area of at least 30 mm² and an aspect ratio of at least about 1:2.

B. The dispenser of claim A wherein the exposure percentage is from 45% to about 90%.

C. The dispenser of claim A or B wherein at least about 65% of the total surface area of the plurality of apertures results from individual apertures of said plurality that each have an area of at least 30 mm².

D. The dispenser of any one of the previous claims wherein the individual apertures have an area of at least about 40 mm².

E. The dispenser of any one of the previous claims wherein the individual apertures have an aspect ratio of at least about 1:2.

F. The dispenser of any one of the previous claims wherein said gap is from 0.5 mm to about 8 mm in height.

G. The dispenser of any one of the previous claims wherein one or both of said first and second walls are convex shaped.

H. The dispenser of claim G wherein said first and second walls form an elliptical shaped disk when joined.

I. The dispenser of claim G wherein said first and second walls form a sphere when joined.

J. The dispenser of claim A wherein an activation button is disposed on said first or second wall.

K. The dispenser of claim J wherein said activation button is situated next to said membrane such that depression of said button activates release of said volatile composition from said cartridge.

L. A method of delivering a volatile composition wherein said method comprises the step of providing a dispenser according to claim A.

M. A volatile composition dispenser comprising:
a) a housing having opposing first and second walls that are joined along their peripheries to one another, wherein said first wall has an aperture and wherein said second wall has a plurality of apertures wherein at least about 60% of a total surface area of the plurality of apertures results from individual apertures that have an aspect ratio of greater than 1:2;
b) a volatile composition cartridge comprising a membrane wherein said cartridge is disposed within the housing between said first and second walls; and
c) a gap, which exists between said cartridge and a bottom surface of the housing, wherein said bottom surface is formed from a joinder of a base portion of one or both of the first and second walls; and
wherein said dispenser is activated by a user and thirty days after said activation, there is about 70% to 90% weight loss of said volatile composition of a partially exposed membrane of a fully exposed membrane.

N. The dispenser of claim M wherein at least about 70% of a total surface area of the plurality of apertures results from individual apertures that have an aspect ratio of greater than 1:2.

O. The dispenser of claim M wherein the individual apertures that have an aspect ratio of greater than 1:4.

P. The dispenser of claim M wherein one or both of said first and second walls are convex shaped.

Q. The dispenser of claim M wherein an activation button is disposed on said first or second wall.

R. The dispenser of claim M wherein said activation button is situated next to said membrane such that depression of said button activates release of said volatile composition from said cartridge.

S. A method of delivering a volatile composition wherein said method comprises the step of providing a dispenser according to claim M.

The examples illustrate the synergy that results when the exposure percentage falls in the claimed range as a consequence of an appropriate proportion of apertures of the plurality of apertures of the second wall having an aspect ratio of greater than 1:2. These same examples illustrate that the desired volatile composition percentage weight loss results from the claimed combination of characteristic plurality of apertures, primary aperture, gap, and housing.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A volatile composition dispenser comprising:
    a) a housing having opposing first and second walls that are joined along their peripheries to one another, wherein said first wall has a primary aperture and wherein said second wall has a plurality of apertures;
    b) a volatile composition cartridge disposed within the housing between said first and second walls, wherein the volatile composition cartridge comprises a receptable containing a volatile composition;
    c) a gap, which exists between said cartridge and a bottom surface of the housing, wherein said bottom surface is formed from a joinder of a base portion of one or both of the first and second walls, and
wherein, upon activation, the exposure percentage is from about 40% to about 90%; wherein at least about 60% of the total surface area of the plurality of apertures results from individual apertures of said plurality that each have an area of at least 30 mm² and an aspect ratio of at least about 1:2, wherein the primary aperature is disposed in the base portion of the first wall, and wherein the volatile composition dispenser further comprises a window, wherein the receptacle is shaped to correspond to a shape of the window.

2. The dispenser of claim 1 wherein the exposure percentage is from 45% to about 90%.

3. The dispenser of claim 1 wherein at least about 65% of the total surface area of the plurality of apertures results from individual apertures of said plurality that each have an area of at least 30 mm².

4. The dispenser of claim 1 wherein the individual apertures have an area of at least about 40 mm².

5. The dispenser of claim 1 wherein the individual apertures have an aspect ratio of at least about 1:2.

6. The dispenser of claim 1 wherein said gap is from 0.5 mm to about 8 mm in height.

7. The dispenser of claim 1 wherein one or both of said first and second walls are convex shaped.

8. The dispenser of claim 7 wherein said first and second walls form an elliptical shaped disk when joined.

9. The dispenser of claim 7 wherein said first and second walls form a sphere when joined.

10. The dispenser of claim 1 wherein an activation button is disposed on said first or second wall.

11. The dispenser of claim 10 wherein said activation button is situated next to said membrane such that depression of said button activates release of said volatile composition from said cartridge.

12. The dispenser of claim 1 wherein one or both of said first and second walls are convex shaped.

13. The dispenser of claim 1 wherein an activation button is disposed on said first or second wall.

14. A method of delivering a volatile composition wherein said method comprises the step of providing a dispenser, the dispenser comprising:
    a) a housing having opposing first and second walls that are joined along their peripheries to one another, wherein said first wall has a primary aperture and wherein said second wall has a plurality of aperatures;
    b) a volatile composition cartridge disposed within the housing between said first and second walls, wherein the volatile composition cartridge comprises a receptable containing a volatile composition;
    c) a gap, which exists between said cartridge and a bottom surface of the housing, wherein said bottom surface is formed from a joinder of a base portion of one or both of the first and second walls, and
wherein, upon activation, the exposure percentage is from about 40% to about 90%; wherein at least about 60% of total surface area of the plurality of aperatures results from individual aperatures of said plurality that each have an area of at least 30 mm² and an aspect ratio of at least about 1:2, wherein the primary aperature is disposed in the base portion of the first wall, and wherein the volatile composition dispenser further comprises a window, wherein the receptable is shaped to correspond to a shape of the window.

15. A volatile composition dispenser comprising:
    a) a housing having opposing first and second walls that are joined along their peripheries to one another, wherein said first wall has a primary aperture and wherein said second wall has a plurality of apertures wherein at least about 60% of a total surface area of the plurality of apertures results from individual apertures that have an aspect ratio of greater than 1:2;

b) a volatile composition cartridge comprising a membrane wherein said cartridge is disposed within the housing between said first and second walls, wherein the volatile composition cartridge comprises a receptable containing a volatile composition; and c) a gap, which exists between said cartridge and a bottom surface of the housing, wherein said bottom surface is formed from a joinder of a base portion of one or both of the first and second walls; and wherein said dispenser is activated by a user and thirty days after said activation, there is about 70% to 90% weight loss of said volatile composition of a partially exposed membrane of a fully exposed membrane, wherein the primary aperature is disposed in the base portion of the first wall, and wherein the volatile composition dispenser further comprises a window, wherein the receptable is shaped to correspond to a shape of the window.

16. The dispenser of claim 15 wherein at least about 70% of a total surface area of the plurality of aperatures results from individual aperatures that have an aspect ratio of greater than 1:2.

17. The dispenser of claim 15 wherein the individual aperatures that have an aspect ratio of greater than 1:4.

18. The dispenser of claim 15 wherein said activation button is situated next to said membrane such that depression of said button activates release of said volatile composition from said cartridge.

* * * * *